(12) United States Patent
Taira et al.

(10) Patent No.: US 8,471,193 B2
(45) Date of Patent: Jun. 25, 2013

(54) PHOTODETECTION DEVICE FOR DETECTING LOW TEMPORAL COHERENCE LIGHT, PHOTODETECTION METHOD, MICROSCOPE AND ENDOSCOPE

(75) Inventors: Kenji Taira, Kodaira (JP); Hiroyoshi Yajima, Sagamihara (JP)

(73) Assignee: Olympus Corporation, Tokyo (JP)

( * ) Notice: Subject to any disclaimer, the term of this patent is extended or adjusted under 35 U.S.C. 154(b) by 318 days.

(21) Appl. No.: 12/743,405

(22) PCT Filed: Mar. 5, 2009

(86) PCT No.: PCT/JP2009/054187
§ 371 (c)(1),
(2), (4) Date: May 18, 2010

(87) PCT Pub. No.: WO2010/100745
PCT Pub. Date: Sep. 10, 2010

(65) Prior Publication Data
US 2011/0049337 A1    Mar. 3, 2011

(51) Int. Cl.
*G01N 21/25* (2006.01)
(52) U.S. Cl.
USPC .................................. 250/227.23; 250/214.1
(58) Field of Classification Search
USPC .............. 250/227.23, 227.21, 227.18, 214 R,
250/214.1; 356/451–458, 460, 484; 359/123,
359/124, 191–195
See application file for complete search history.

(56) References Cited

U.S. PATENT DOCUMENTS 6,441,356 B1    8/2002   Mandella et al.
6,486,958 B1 *  11/2002  Szafraniec et al. ........... 356/484
6,527,708 B1    3/2003   Nakamura et al.
2003/0055342 A1 3/2003  Toida
2004/0109164 A1 6/2004  Horii et al.

FOREIGN PATENT DOCUMENTS

JP    S60-10612 B2   3/1985
JP    02-110346      4/1990
JP    03-111737      5/1991
JP    04-027845      1/1992
JP    6-165784 A     6/1994

(Continued)

OTHER PUBLICATIONS

European Search Report dated Mar. 14, 2012 from corresponding European Patent Application No. EP 09 82 9868.0.
Notice of Reasons for Refusal dated Mar. 5, 2013 from corresponding Japanese Patent Application No. 2010-503162, together with an English language translation.

(Continued)

*Primary Examiner* — Que T Le
(74) *Attorney, Agent, or Firm* — Scully, Scott, Murphy & Presser, P.C.

(57) ABSTRACT

There are provided a photodetection device, a photodetection method, a microscope and an endoscope, which are capable of heterodyne-detecting desired light to be detected with high sensitivity and high S/N ratio, among which the photodetection device includes: a local light generation unit (10) generating local light having a plurality of optical frequency components in an optical frequency band of light to be detected within a given period of time; a light combining unit (20) combining the local light generated from the local light generation unit (10) and the light to be detected; and a photoelectric conversion unit (30) photoelectrically-converting light output from the light combining unit (20) and generating a beat signal of the local light and the light to be detected, such that the light to be detected is heterodyne-detected based on an output of the photoelectric conversion unit (30).

15 Claims, 13 Drawing Sheets

FOREIGN PATENT DOCUMENTS

| | | |
|---|---|---|
| JP | 8-184502 A | 7/1996 |
| JP | 9-297004 A | 11/1997 |
| JP | 2003-90792 A | 3/2003 |
| WO | WO 2008/090599 A1 | 7/2008 |

OTHER PUBLICATIONS

English language abstract of Japanese Patent Application No. JP 53112652 A dated Oct. 2, 1978.

* cited by examiner

PHOTODETECTION DEVICE FOR DETECTING LOW TEMPORAL COHERENCE LIGHT, PHOTODETECTION METHOD, MICROSCOPE AND ENDOSCOPE

TECHNICAL FIELD

This invention relates to a photodetection device and a photodetection method, and a microscope and an endoscope.

BACKGROUND ART

In various systems using light such as of organism observation, a sensor, security, laser radar and the like, the technique of detecting desired signal light (light to be detected) is a fundamental and important element significantly influencing their performance. In particular, the needs for the high-speed high-sensitive detection technique are high.

For example, in organism observation, it is required to perform high-speed photodetection to enable accurate observation since the state and shape of the organism vary with time. Moreover, the organism is easily damaged by optical irradiation, and thus the amount of illumination light or excitation light with which an organism sample is to be irradiated has an upper limit. Therefore, the optical signal obtained from the organism is weak in general. For these reasons, the high-speed high-sensitive photodetection technique is strongly demanded in organism observation using light.

As the currently-used typical photodetection device, there can be mentioned a PMT (Photo Multiplier Tube), an APD (Avalanche Photo Diode) and a PD (Photo Diode). The PMT and the APD perform electron multiplying in the detection device, which enables high-sensitive photodetection. On the other hand, the PD does not have an electron multiplying function in the detection device and thus signals are usually amplified with the use of an electric amplifier, although it achieves a very high response speed. That is, any device of the PMT, the APD and the PD performs signal amplification electrically to improve the sensitivity.

Moreover, there can be mentioned, as the typical two-dimensional photodetector, a CCD (Charged Coupled Device), a CMOS (Complementary Metal Oxide Semiconductor), an EM-CCD (Electron Multiplying-CCD), an EB-CCD (Electron Bombardment-CCD) and an I-CCD (Intensified-CCD). When weak light is to be detected using the CCD or the CMOS, it is necessary, like the PD, to dispose an electric amplifier in a subsequent part so as to improve the sensitivity. The EM-CCD and the EB-CCD have an electron multiplying function in the detection device, like the APD, and achieve the higher sensitivity. The I-CCD has a configuration in which an Image Intensifier (I.I.) is disposed before the CCD. In the I.I, incident optical signals are converted to electrical signals once, and electron multiplying is performed in a MCP (Micro Channel Plate) embedded in the I.I., thereafter the multiplied electrons are rendered to collide with a fluorescent plate so that the multiplied electrical signals are converted to light again. The output light from the I.I. is converted to electrical signals by the CCD. That is, the I-CCD also performs signal amplification in an electric domain, thus achieving high-sensitive photodetection.

In the above conventional photodetection technique using signal amplification in an electric domain, there is a trade-off relation between the speed and the sensitivity, which makes it significantly difficult to achieve both high speed and high sensitivity. Therefore, it is unavoidable in the present situation that either of speed or sensitivity is sacrificed to perform photodetection.

As one of techniques capable of high-speed high-sensitive photodetection, the optical heterodyne detection technique is also widely used. The optical heterodyne detection technique is a photodetection method using interference effects by light to be detected and local light having an optical frequency slightly different from of light to be detected, and the intensity of local light is sufficiently increased so as to detect light to be detected with high sensitivity. Provided that the intensity of local light is sufficient, it is possible to perform ideal photodetection at a shot noise limit even when a high-speed electronic circuit is used. Thus, the high speed and the high sensitivity in photodetection are both achieved. In this case, however, it is general to use, as signal light and local light, lights enabling mutual interference to be stable temporally and spatially.

As a method for improving the temporal coherency, the following two methods are mainly used. The first method is a method in which the output from the same light source is split so that each is used as signal light and local light. In this case, the output of the light source is split, and thus it is arranged so that a relative delay time between signal light and local light before the recombination is shorter than a coherence time of the light source. Thereby, the interference state between signal light and local light becomes temporally stable. It is noted that the optical frequencies of signal light and local light are set to be slightly different from each other with the use of an optical frequency shifter or Doppler shift. This method has been conventionally used since the stable interference state can be achieved relatively easily (see Patent Documents 1, 2, for example).

The second method is a method using two independent light sources in which a line width of optical spectrum is significantly narrow (optical spectrum purity is significantly high) and an optical frequency is stabilized with high accuracy. These two independent light sources are used respectively as signal light or local light. In this case, the optical frequencies of signal light and local light are set to be slightly different from each other. This method has been conventionally very difficult to achieve because of technical constraints. However, since the recent technical development has made it possible to obtain a laser in which the optical spectrum purity is significantly high with a width of optical spectrum line being about kHz and an optical frequency is stabilized with high accuracy, the second method also enables a relatively stable interference state recently.

On the other hand, a spatial mode filter such as a confocal optical system or the like is used at the signal light side in order to improve the spatial coherency. Thus, only signal light components having the high coherency with local light are spatially extracted and used for optical heterodyne detection.

Patent Document 1: JP 06-21868 B2
Patent Document 2: JP 07-21452 B2

DISCLOSURE OF THE INVENTION

Problems to be Solved by the Invention

However, signal light detected in organism observation, a sensor, security, laser radar and the like does not have the high temporal coherence as laser light does, and it is quite often the case that it has the low temporal coherence, that is, a broad line width of optical spectrum as lamp light, fluorescence and the like do. Moreover, even when laser light is used for spectroscopic measurement or the like, the line width of an optical spectrum is intentionally expanded so as to avoid influences by speckles particularly in measurement of a scattering medium. That is, in spectroscopic measurement or the like, there is used laser light with an optical spectrum line width capable of securing the accuracy of the optical frequency to some degree and avoiding influences by speckles.

According to the above conventional method, therefore, it is necessary to perform detection under conditions where the generation source of signal light and local light is the same and the relative delay time between signal light and local light is shorter than the coherence time thereof.

For example, when light has a central optical frequency of 600 THz (wavelength of 500 nm) and an optical spectrum line width of 120 THz (wavelength width of about 100 nm), the coherence time is about $1.0 \times 10^{-14}$ seconds (which corresponds to about $3.0 \times 10^{-6}$ m in spatial distance in vacuum) and the allowed delay time between signal light and local light is significantly short.

Moreover, considering also laser light whose line width has been intentionally expanded so that a central optical frequency is 600 THz and an optical spectrum line width is 120 GHz (wavelength width is about 100 pm), the coherence time is about $1.0 \times 10^{-11}$ seconds (which corresponds to about $3.0 \times 10^{-3}$ m in spatial distance in vacuum) and the allowed relative delay time is still short.

As above, the temporal and spatial likelihood is small under the condition where the allowed relative delay time is small, which limits the use of heterodyne detection very strictly.

Moreover, when signal light (light to be detected) is temporally low-coherence light newly generated in a sample such as fluorescence or the like, local light suitable for high sensitive heterodyne detection can not be prepared.

For the above reasons, when temporally low-coherence optical signals have been heterodyne-detected, the stable interference state cannot be maintained, conventionally resulting in a situation where the high-speed high-sensitive photodetection is difficult to achieve.

Therefore, an object of the invention made focusing on these points is to provide a photodetection device and a photodetection method and a microscope and an endoscope capable of heterodyne-detecting desired light to be detected with high sensitivity and high SN (Signal to Noise) ratio.

SUMMARY OF THE INVENTION

A first aspect of the invention for achieving the above object is a photodetection device, comprising a local light generation means generating local light having a plurality of optical frequency components in an optical frequency band of light to be detected within a given period of time;

a light combining means combining the local light generated from the local light generation means and the light to be detected; and a photoelectric conversion means photoelectrically-converting light output from the light combining means and generating a beat signal of the local light and the light to be detected, wherein the light to be detected is heterodyne-detected based on an output of the photoelectric conversion means.

A second aspect of the invention is a photodetection device according to the first aspect, wherein the local light generation means comprises a plurality of light generation sources generating continuous light with a respectively different optical frequency.

A third aspect of the invention is a photodetection device according to the first aspect, wherein the local light generation means is constituted by an optical pulse generation means generating an optical pulse train.

A fourth aspect of the invention is a photodetection device according to the third aspect, wherein the local light generation means further comprises an optical filter means selecting given optical frequency components as local light from output light of the optical pulse generation means.

A fifth aspect of the invention is a photodetection device according to the third aspect, wherein the local light generation means further comprises an optical spectrum shaping means shaping a spectrum of output light of the optical pulse generation means.

A sixth aspect of the invention is a photodetection device according to the third aspect, wherein the local light generation means further comprises an optical spectrum broadening means broadening a spectrum of output light of the optical pulse generation means.

A seventh aspect of the invention is a photodetection device according to the sixth aspect, wherein the local light generation means further comprises an optical filter means selecting given optical frequency components as local light from output light of the optical spectrum broadening means.

An eighth aspect of the invention is a photodetection device according to the sixth aspect, wherein the local light generation means further comprises an optical spectrum shaping means shaping a spectrum of output light of the optical spectrum broadening means.

A ninth aspect of the invention is a photodetection device according to any one of the third to eighth aspect, wherein the optical pulse generation means generates the optical pulse train at a repetition rate being twice or more a signal processing frequency band processing an output of the photoelectric conversion means.

A tenth aspect of the invention is a photodetection device according to any one of the third to ninth aspect, wherein the optical pulse generation means comprises a mode-locked laser.

An eleventh aspect of the invention is a photodetection device according to any one of the third to ninth aspect, wherein the optical pulse generation means comprises a gain-switched laser or a Q-switched laser.

A twelfth aspect of the invention is a photodetection device according to any one of the first to eleventh aspect, further comprising an envelope detection means detecting an envelope of an output of the photoelectric conversion means.

A thirteenth aspect of the invention for achieving the above object is a photodetection method, comprising a local light generation step generating local light having a plurality of optical frequency components in an optical frequency band of light to be detected within a given period of time;

a combining step combining the light to be detected and the local light; and a photoelectric conversion step photoelectrically-converting the combined light and generating a beat signal of the local light and the light to be detected, wherein the light to be detected is heterodyne-detected based on the beat signal.

A fourteenth aspect of the invention for achieving the above object is a microscope detecting light to be detected from a sample to be observed, comprising a photodetection device according to any one of claims 1 to 12, wherein the photodetection device heterodyne-detects the light to be detected from the sample to be observed.

A fifteenth aspect of the invention for achieving the above object is an endoscope detecting light to be detected from an inside of a body cavity and observing the inside of the body cavity, comprising a photodetection device according to any one of claims 1 to 12,
wherein the photodetection device heterodyne-detects the light to be detected from the inside of the body cavity.

Effect of the Invention

According to the photodetection device or the photodetection method of the invention, a plurality of beat signals is generated from light to be detected and local light having a plurality of optical frequency components in an optical frequency band of light to be detected within a given period of time, and those signals are added so as to heterodyne-detect light to be detected, which makes it possible to detect desired light to be detected with high sensitivity and high S/N ratio even when an object to be inspected is one in which the scattering by scattering body such as an organism or the like decreases light to be detected. Moreover, it becomes possible to detect, with high sensitivity and high SNR, light to be detected not only from scattering body but also from substances to be detected existent in a deep portion of an object to be detected or far portion therefrom or substances to be detected existent under circumstances where other light absorbing substances mediate.

According to the microscope of the invention, moreover, the above photodetection device heterodyne-detects light to be detected from a sample to be observed by combining the light with local light having a plurality of optical frequency components in an optical frequency band of light to be detected within a given period of time, which makes it possible to observe the sample to be observed with high sensitivity and high S/N ratio.

According to the endoscope of the invention, the above photodetection device heterodyne-detects light to be detected from the inside of a body cavity by combining the light with local light having a plurality of optical frequency components in an optical frequency band of light to be detected within a given period of time, which makes it possible to observe the inside of the body cavity with high sensitivity and high S/N ratio.

Figure 1:
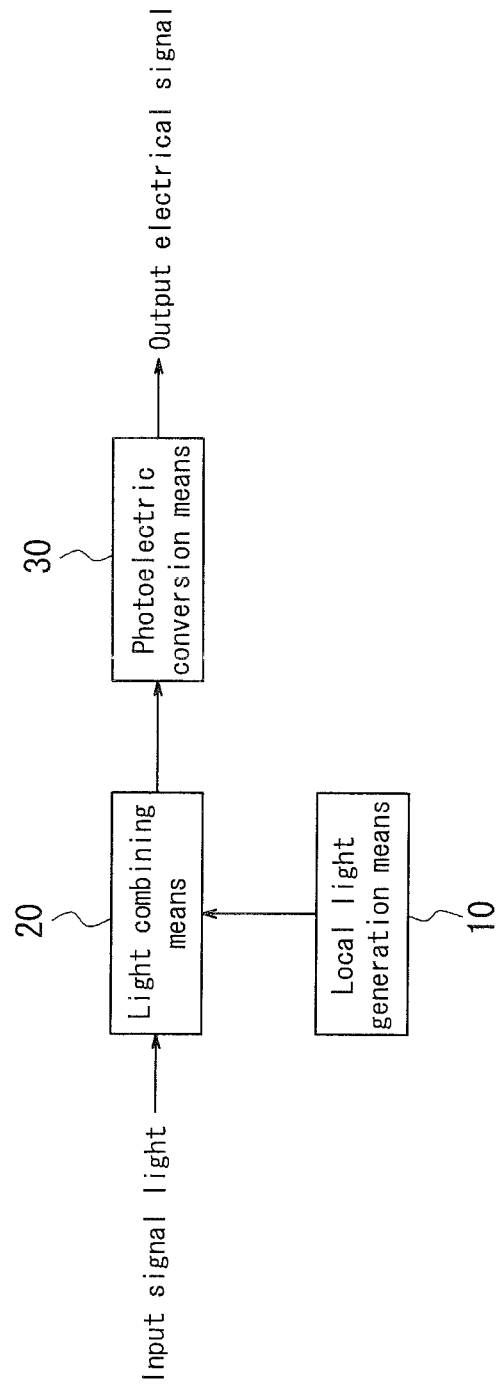
FIG. 1 is a block diagram illustrating a basic configuration of the photodetection device according to the first embodiment of the invention.

REFERENCE SYMBOLS 10 local light generation means
20 light combining means
30 photoelectric conversion means
41 Ar laser
42 intensity modulator
43 X-Y galvano scanner mirror
46 dichroic minor
47 objective lens
48 living cell sample
49 half mirror
51 DPSS laser
52 Er-doped fluoride fiber laser
53 dichroic mirror
61 DBD (differential detector)
62 envelope detection circuit
63 electric amplifier
64 AD converter
65 computer
66 monitor
70 pulse light generation means
80 optical frequency selection means
90 optical spectrum shaping means
100 optical spectrum broadening means
111 Xe lamp
112 computer
115 illuminating lens
116 organism sample
117 collective lens
118 combining mirror
121 gain-switched laser diode
125 PCF (photonic crystal fiber)
126 collimate lens
128 collective lens
130 two-dimensional CCD array
131 AD converter
132 DSP (digital signal processor)
133 monitor
134 housing
151 Xe lamp
152 computer
155 collimator
156 organism sample
157 collective lens
158 scanning mount
160 housing
161 Titanium-sapphire laser
162 PCF
163 optical filter
164 optical fiber coupler 165 DBD
166 electric amplifier
167 AD converter
168 monitor
171 Titanium-sapphire laser
172 partially reflective mirror
174 PCF
175 intensity modulator
177 optical spectrum shaping filter
180 half mirror
181 X-Y galvano scanner mirror
184 dichroic mirror
185 objective lens
186 living cell sample
191 DBD
192 envelope detection circuit
193 electric amplifier
194 AD converter
195 computer
196 monitor

BEST MODE FOR CARRYING OUT THE INVENTION

Embodiments of the invention will be described below with reference to the accompanying drawings.

First Embodiment

FIG. 1 is a block diagram illustrating a basic configuration of the photodetection device according to the first embodiment of the invention. The photodetection device uses a local light generation means 10 generating local light having a plurality of frequency components in a frequency band of input signal light (light to be detected) within a given period of time, and combines the local light from the local light generation means 10 with the input signal light at a light combining means 20. Then, the photodetection device converts the combined light to electrical signals at a photoelectric conversion means 30, to obtain signals to which a plurality of beat signals has been added, thus heterodyne-detects input signal light.

As the local light generation means 10, there is used, for example, a plurality of monochromatic light sources, a light source in which an amplitude, a phase or an optical frequency has been modulated, an optical frequency comb oscillator, or an optical pulse source or the like, for example, so as to generate local light having a plurality of optical frequency components in an optical frequency band of input signal light within a given period of time. The light combining means 20 is constituted using a dielectric multilayer half mirror, a fiber optical coupler, a flat waveguide optical coupler or the like, for example. Moreover, there may be disposed a spatial mode filter adjusting a spatial mode of input signal light or local light before the light combining means 20, if necessary. The photoelectric conversion means 30 is constituted using the PMT, the APD, the PD, the CCD, the CMOS, the EM-CCD, the EB-CCD or the like, for example. Moreover, the photoelectric conversion means 30 can be constituted using that of Dual-Balanced-Detection (DBD) type removing direct-current components and the intensity fluctuation of signal light and local light.

Input signal light as light to be detected is detected using, in particular, amplitude information and intensity information in electrical signals output from the photoelectric conversion means 30. Such information is obtained by envelope detection, square-law detection, synchronous detection or the like.

When the DBD type is not used for the photoelectric conversion means 30, it is effective to add a filter means removing direct-current components.

Figure 2:
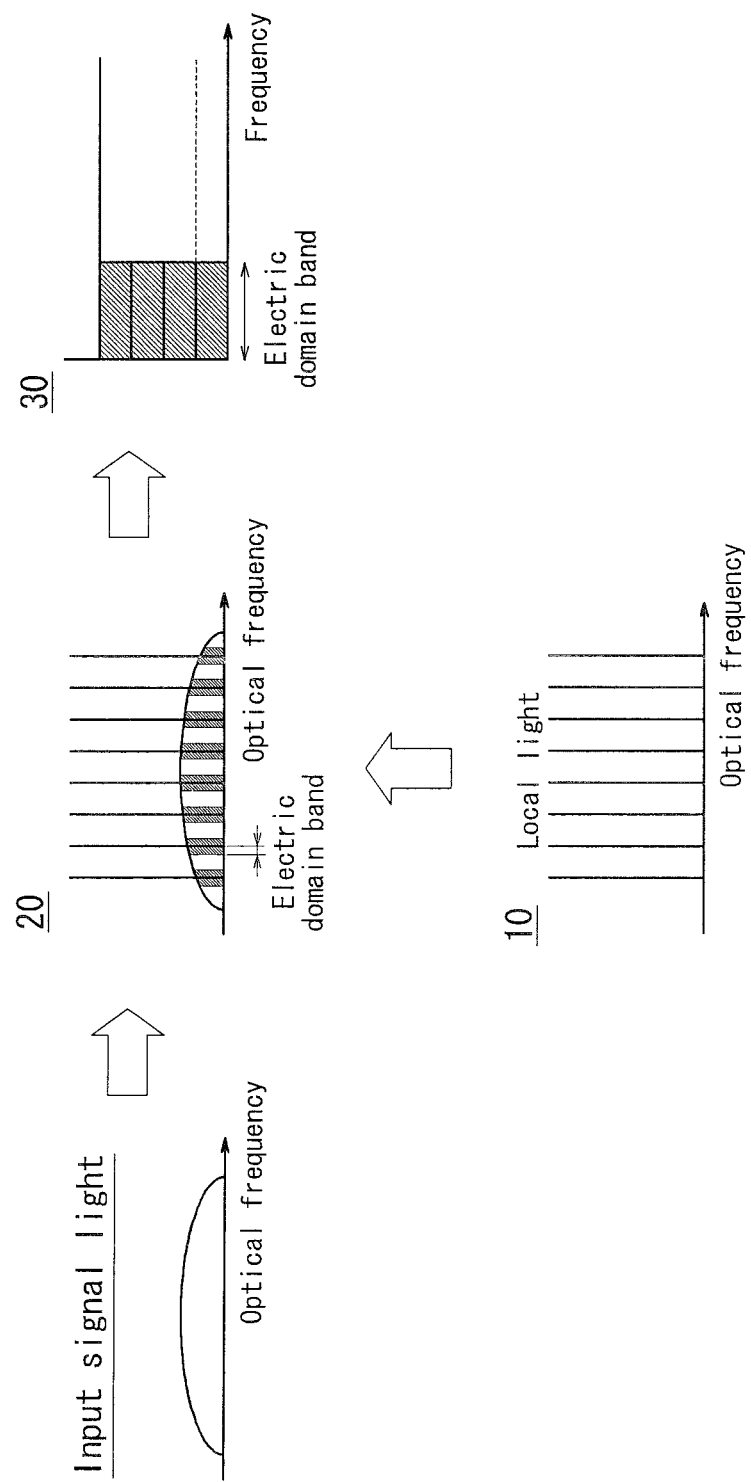
FIG. 2 is a schematic diagram illustrating operation of the photodetection device shown in FIG. 1.

FIG. 2 is a schematic diagram illustrating operation of the photodetection device shown in FIG. 1. As shown in the diagram, in the photodetection device according to the embodiment, an optical frequency of local light having a plurality of optical frequencies generated from the local light generation means 10 within a given period of time is set to be included within an optical spectrum line width of input signal light, and the input signal light and the local light are combined at the light combining means 20. Then, the photodetection device photoelectrically-converts the combined light at the photoelectric conversion means 30, to obtain output to which a plurality of beat signals has been added, thus heterodyne-detects the input light signal by using the amplitude information. That is, there is used, as local light, one having a plurality of optical frequency components within a given period of time so as to optical-heterodyne-detect input signal light having the temporally low coherence, that is, a wide optical spectrum line width. In this case, beat signals are noise-like, and thus the amplitude information of such noise-like beat signals is rendered to be detected signals.

Here, each interval between a plurality of optical frequencies of local light generated from the local light generation means 10 is twice or more the electric band in the whole photodetection system. In this case, beat signals of the input signal light and local light with a certain optical frequency do not correlate with beat signals of the input signal light and local light with another optical frequency. Therefore, these beat signals are added incoherently by the photoelectric conversion means 30. That is, the amplitude of beat signals to be detected becomes larger by using local light having a plurality of optical frequency components, as compared with a case using local light having only one kind of optical frequency component. There is thus achieved high-sensitive optical heterodyne detection which has not been achieved conventionally. Moreover, the use of local light having sufficiently high optical power makes high-speed high-sensitive photodetection possible.

It is noted that electrical signals output from the photoelectric conversion means 30 are signals whose carrier frequency is not determined. Moreover, various frequency components are included, which broadens a frequency band used. Thus, the expansion of frequency band used allows a lot of noises to be mixed, causing the deterioration of photodetection sensitivity. Therefore, in order to obtain information of light to be detected from output of the photoelectric conversion means 30, it is particularly preferable to conduct envelope detection. As above, it is arranged that information of light to be detected is obtained by envelope detection, which makes it possible to prevent the mixture of noises by limiting bands used and to cut the cost of components constituting the device in accordance with reduction of frequency bands.

Second Embodiment

Figure 3:
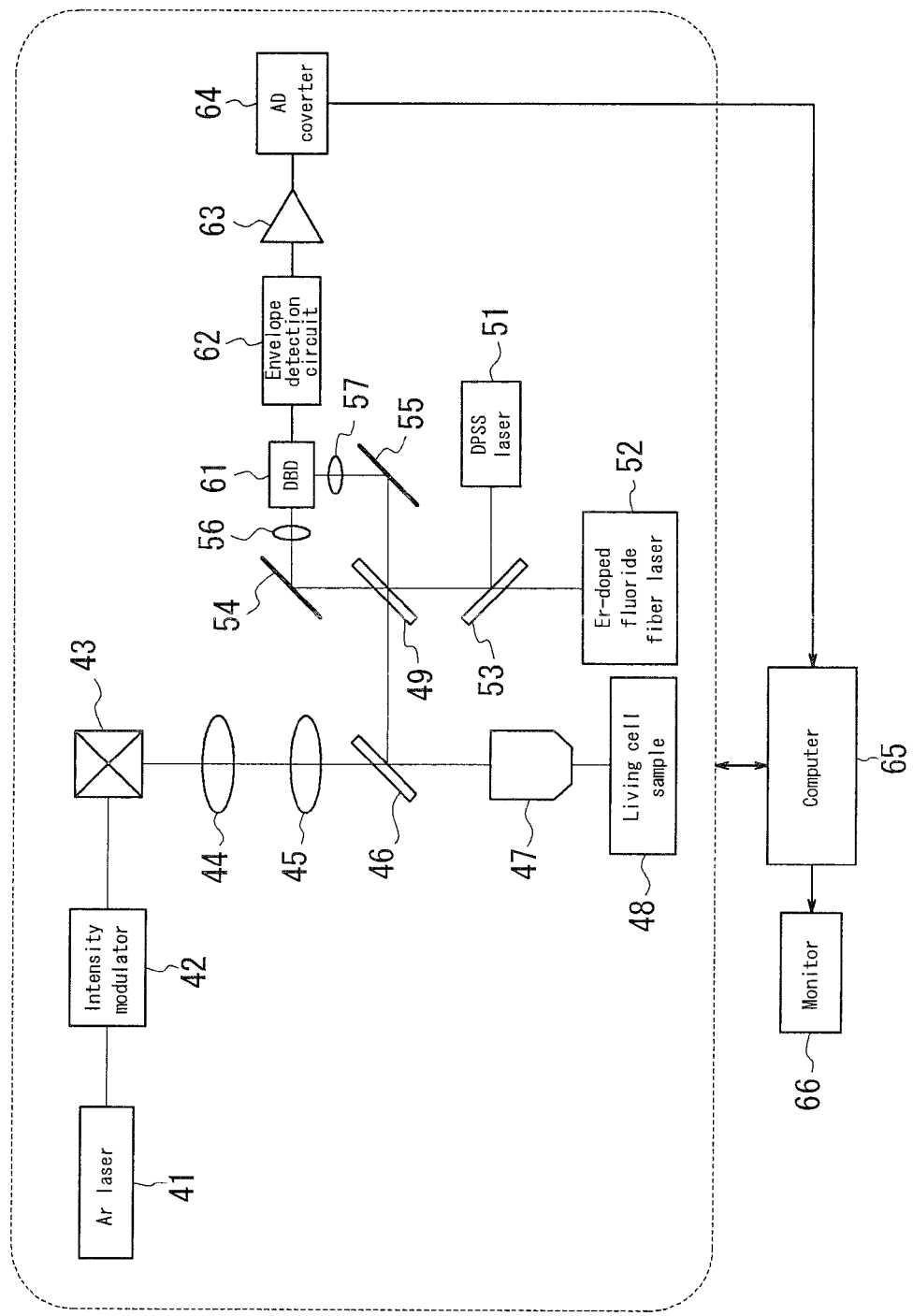
FIG. 3 is a block diagram illustrating a configuration of a main part of the laser scanning fluorescence microscope according to the second embodiment of the invention.

FIG. 3 is a block diagram illustrating a configuration of a main part of the laser scanning fluorescence microscope according to the second embodiment of the invention. The laser scanning fluorescence microscope has, as the excitation light source, an Ar laser 41 continuously oscillating at a wavelength of 488 nm. In FIG. 3, with respect to laser light emitted from the Ar laser 41, its light intensity is adjusted by a light intensity modulator 42 such as an Acousto Optic Modulator (AOM) or the like, for example, thereafter the resulting light passes through an X-Y galvano scanner mirror 43, a pupil lens 44, a tube lens 45, a dichroic mirror 46 and an objective lens 47, and is collected so that a living cell sample 48 to be inspected is irradiated therewith. Thus, in the laser scanning fluorescence microscope, the light intensity modulator 42, the X-Y galvano scanner mirror 43, the pupil lens 44, the tube lens 45, the dichroic mirror 46 and the objective lens 47 constitute the light irradiation means irradiating a sample with excitation light from the excitation light source. Moreover, the X-Y galvano scanner mirror 43 constitutes the light scan means.

It is noted that there is used, as the living cell sample 48, an object to be inspected dyed with fluorescent dye or an object to be inspected in which fluorescent protein is expressed. Here, there is used an object to be inspected in which fluorescent protein eGFP (enhanced Green Fluorescence Protein) is expressed. Therefore, when the living cell sample 48 is irradiated with laser light from the Ar laser 41, eGFP is excited and then fluorescence having a wavelength of about 500 nm to 600 nm is generated.

The fluorescence generated from the living cell sample 48 passes through the objective lens 47 to the dichroic mirror 46. The dichroic mirror 46 is configured so as to allow light having a wavelength of 488 nm to pass therethrough and so as to reflect light having a wavelength longer than 500 nm. Thus, fluorescence having a wavelength of about 500 nm to 600 nm generated in the living cell sample 48 is reflected by the dichroic mirror 46.

The fluorescence reflected by the dichroic mirror 46 is combined with local light by a half mirror 49 as the light combining means. There is used, as local light, one in which laser light emitted from a DPSS (Diode Pumped Solid State) laser 51 and laser light emitted from an Er-doped fluoride fiber laser 52 are combined by the dichroic mirror 53. As the DPSS laser 51, there is used, for example, one continuously oscillating in a single spatial mode at a wavelength of 532 nm and capable of output with an optical average power of not higher than 10 mW. Moreover, as the Er-doped fluoride fiber laser 52, there is used, for example, one continuously oscillating in a single spatial mode at a wavelength of 543 nm and capable of output with an optical average power of 10 mW.

That is, in the embodiment, the local light generation means is constituted using two continuous-wave lasers of the DPSS laser 51 and the Er-doped fluoride fiber laser 52.

Two combined output obtained from the half mirror 49 are reflected by a reflective mirror 54, 55, respectively and input, through a lens 56, 57, to a DBD (Dual Balanced Detector) 61 as the photoelectric conversion means constituted by an SiPD (Silicon Photo Diode), then being photoelectrically-converted. The electrical signals output from the DBD 61 are envelope-detected at an envelope detection circuit 62, then amplified by an electric amplifier 63, and further converted by an AD converter 64 from analog signals to digital signals to be supplied to a computer 65.

The computer 65 controls the whole of laser scanning fluorescence microscope. Thus, laser light from the Ar laser 41 is deflected by the X-Y galvano scanner mirror 43, and the living cell sample 48 is two-dimensionally scanned in a plane perpendicular to a light axis from the objective lens 47. Then, the output obtained from the AD converter 64 is processed at each scanned point, and a fluorescence image is displayed on a monitor 66.

Thus, the laser scanning fluorescence microscope according to the embodiment heterodyne-detects fluorescence generated from the living cell sample 48 through irradiation of laser light from the Ar laser 41 with the use of local light obtained from the DPSS laser 51 and the Er-doped fluoride fiber laser 52 having a sufficiently high optical power. Therefore, even if fluorescence as signal light obtained from the living cell sample 48 is weak, it is possible to photoelectrically-convert fluorescence at high speed and with high sensitivity with the use of the DBD 61 constituted by the SiPD without increasing the optical power of laser light with which the living cell sample 48 is to be irradiated and without extending a reception accumulated time, thus enabling fluorescence observation of the living cell sample 48 with high sensitivity and high S/N ratio.

Moreover, a single-spatial-mode light source is used as local light, which makes it possible to collect local light to the degree of almost diffraction limit on the light receiving surface of the DBD 61. With respect to the fluorescence and local light generated from the living cell sample 48, only spatially-overlapped parts thereof on the light receiving surface of the DBD 61 are detected as beat signals, and thus it is possible to achieve confocal effects although the laser scanning fluorescence microscope of the embodiment does not have a confocal pinhole.

Furthermore, there are used, as the local light generation means, two continuous-wave lasers of the DPSS laser 51 and the Er-doped fluoride fiber laser 52, which enables a laser scanning fluorescence microscope having a high degree of freedom according to an optical frequency band or an optical spectrum shape of light to be detected particularly by selecting the intensity or the optical frequency of each light source. Moreover, in the embodiment, light to be detected is of temporally low coherence. Thus, the needs for the optical frequency stability of local light are not high. Moreover, beat signals to be detected are noise-like signals for which a carrier frequency cannot be defined, which makes it unnecessary to fix the frequency interval between local lights and light to be detected although the fixing has been essential in the conventional method. Furthermore, as long as the frequency interval between local light is set to be wider than the electric band of the whole photodetection system, beat signals between local light are not detected. Therefore, the restriction for the stability of the optical frequency of the local light generation means is loose. Therefore, a very low cost continuous-wave laser can be used as the local light source. It is noted that the number of continuous-wave light sources constituting the local light generation means is not limited to two, and may be three or more according to a band of input signal light to be detected.

Third Embodiment

Figure 4:
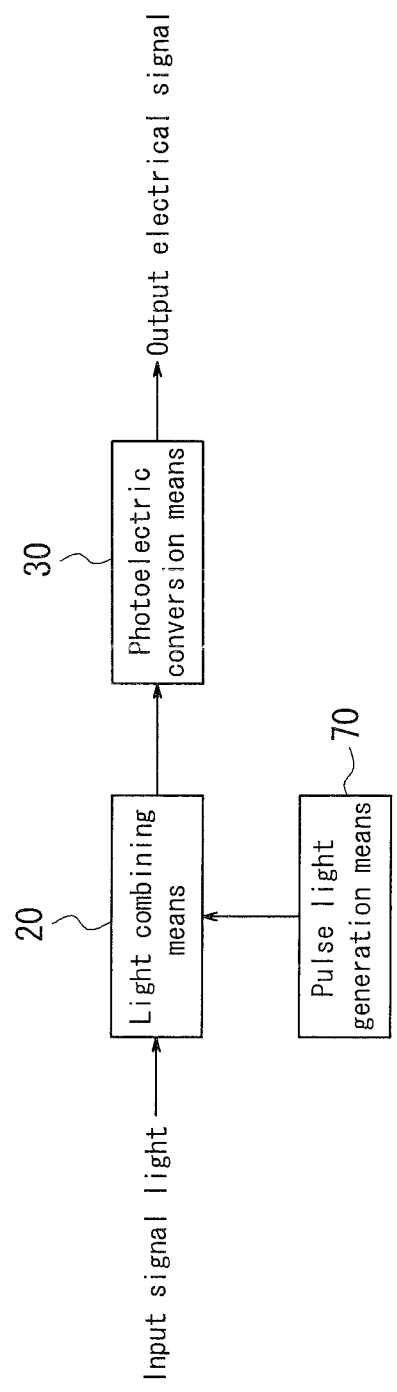
FIG. 4 is a block diagram illustrating a configuration of a main part of the photodetection device according to the third embodiment of the invention.

FIG. 4 is a block diagram illustrating a configuration of a main part of the photodetection device according to the third embodiment of the invention. With respect to the photodetection device, in the configuration shown in FIG. 1, the local light generation means 10 is constituted by a pulse light generation means 70. The pulse light generation means 70 is constituted by combination of an optical pulse source such as a mode locked laser, a gain-switched laser, a Q-switched laser or the like and an optical delay generator, a chirp generator, an optical amplifier, an optical frequency converter or the like, for example. Here, the optical delay generator is a spatial delay circuit or the like constituted by an optical fiber delay line, a mirror or the like, for example. The chirp generator is one using a pair of diffraction gratings, a pair of prisms, a chirped fiber Bragg grating or a spatial liquid crystal modulator or an optical fiber or the like, for example. The optical amplifier is a rare-earth-doped optical fiber amplifier, an optical fiber amplifier using stimulated Raman scattering effects, an optical parametric amplifier, a semiconductor optical amplifier or the like, for example. The optical frequency converter is one using a second harmonic generation (SHG), a third harmonic generation (THG) or a four wave mixing (FWM) effects or stimulated Raman scattering effects, or the like. It is noted that the repetition rate of the pulse train output from the pulse light generation means 70 is set to be twice or more the signal processing frequency band and preferably twice the signal processing frequency band. Since other configurations are the same as in FIG. 1, the same components are represented with the same reference symbols, and the description thereof will be omitted.

As above, when the local light generation means is constituted by the pulse light generation means 70, the light spectrum of the optical pulse train generated from the pulse light generation means 70 has a structure in which the optical frequency is existent in the frequency spacing corresponding with of the repetition rate of the optical pulse train in an optical spectrum band, which makes it possible to easily obtain a large amount of local light having different optical frequencies. Moreover, the optical pulse train with a narrow time width has a broad optical spectrum band, which makes it possible to detect light to be detected with very high sensitivity even when the light is of wide bandwidth. Furthermore, when the pulse light generation means 70 is used, local light having a lot of optical frequencies can be obtained with its simple configuration, which makes the management of the light source significantly easy and enables the compact construction of the local light generation means. In addition, beat signals of signal light temporally-overlapping with the optical pulse as local light are detected. Thus, the timing of the optical pulse is adjusted, which enables the time-resolution measurement having the time resolution which is comparable to the optical pulse time width.

Moreover, when the pulse light generation means 70 is constituted using a mode locked laser, a relative intensity fluctuation between each of frequency components of local light can be rendered to be significantly small, thus enabling very low noise photodetection. That is, when local light including a lot of optical frequency components is used, the fluctuation of the relative intensity between each of optical frequency components also causes the fluctuation of the beat signal intensity, thus resulting in noises at the time of detection. In this aspect, the mode locked laser can generate a very low noise optical pulse train, which can make the optical spectrum purity of each optical frequency component included in a light spectrum significantly high, and make the fluctuation of relative intensity between each of frequency components significantly small.

Moreover, when the pulse light generation means 70 is constituted using a gain-switched laser or a Q-switched laser, a desired frequency interval of optical frequency components can be achieved, thus enabling the constant adjustment to desired sensitivity, even when the measurement velocity is varied, according to the variation. That is, the frequency interval of optical frequency components included in a light spectrum of an optical pulse train is equal to a repetition rate of the optical pulse train, as described above. The frequency interval of the optical frequency components is preferable to be close to the extent that it is not within the range of the electric band of whole photodetection system, in terms of detection sensitivity. In this respect, when a gain-switched laser or a Q-switched laser is used, the repetition rate of optical pulse train can be easily changed, which makes it possible to easily change a frequency interval of optical frequency components included in local light. Thus, even when a measurement velocity is varied, it becomes possible to constantly adjust to the desired sensitivity according to the variation.

Furthermore, the repetition rate of the pulse train output from the pulse light generation means 70 is set to be twice the signal processing frequency band, which enables high-sensitive detection without detection signal output being influenced by the phase relation of adjacent optical frequency components of local light. That is, in the light spectrum of the optical pulse train used as local light, optical frequency components are existent at intervals of the repetition rate. The phase relation between each of optical frequency components has the strong correlation, and thus the optical frequency component of signal light positioned in the middle of adjacent optical frequency components of local light is coherently added in an electric domain. That is, the detection signal output is varied depending on the phase relation of adjacent optical frequency components. In order to avoid this, there occurs a necessity of managing the phase relation between each optical frequency component of the optical pulse train used as local light. In this respect, the repetition rate of the optical pulse train output from the pulse light generation means 70 is set to twice or more the signal processing frequency, which can solve the above problem of output variation. Then, the repetition rate of the optical pulse train is preferably set to be twice the signal processing frequency, which makes the interval of each optical frequency component of local light close, thus enabling high-sensitive photodetection.

Fourth Embodiment

Figure 5:
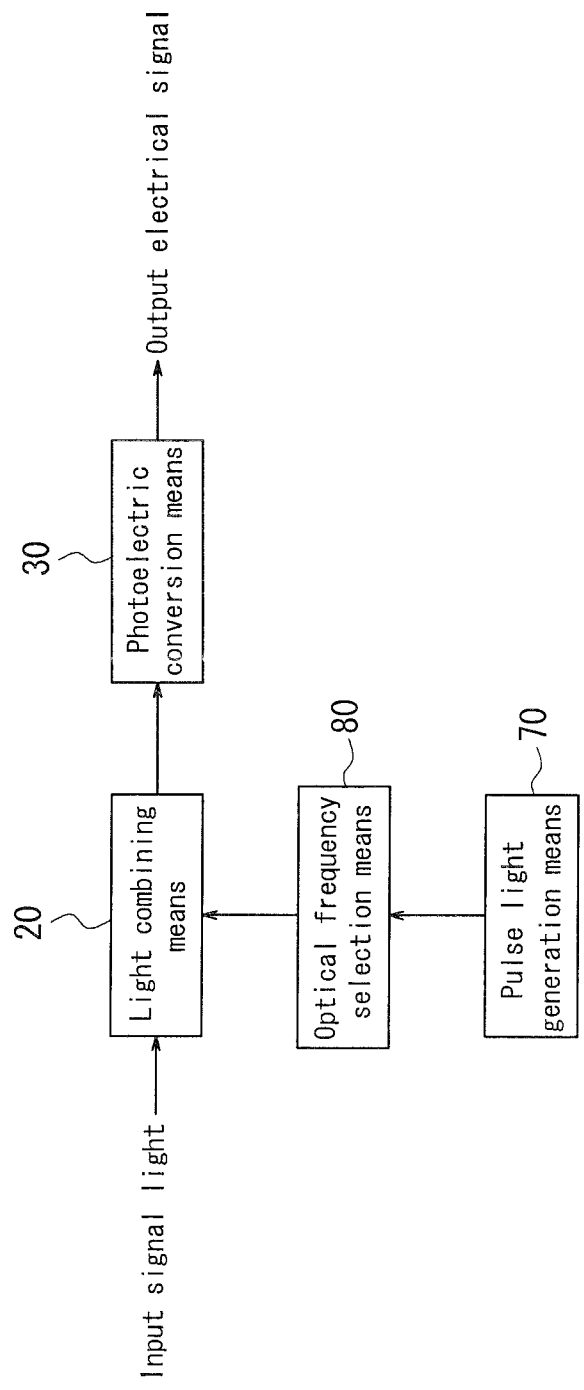
FIG. 5 is a block diagram illustrating a configuration of a main part of the photodetection device according to the fourth embodiment of the invention.

FIG. 5 is a block diagram illustrating a configuration of a main part of the photodetection device according to the fourth embodiment of the invention. With respect to the photodetection device, in the photodetection device having the configuration shown in FIG. 4, there is disposed, between the pulse light generation means 70 and the light combining means 20, an optical frequency selection means 80 selecting one part of optical frequencies from output light of the pulse light generation means 70 and outputting them as local light to the light combining means 20.

The optical frequency selection means 80 is constituted using a dielectric multilayer filter, a light absorption filter, a diffraction grating filter, a prism filter, a grism filter, a VIPA (Virtually Imaged Phased Array) filter, an AWG (Arrayed Wave Guide) filter, a FBG (Fiber Bragg Grating) filter or the like. Since other configurations are the same as in FIG. 1, the same components are represented with the same reference symbols, and the description thereof will be omitted.

As above, when the optical frequency selection means 80 is provided after the pulse light generation means 70, the optical frequency selection means 80 can remove local light which does not contribute to photodetection in the case where the light spectrum of the optical pulse train output from the pulse light generation means 70 is wider than the optical spectrum band of light to be detected, which can reduce mixture of excessive noises and thus detect a desired signal to be detected with high sensitivity and high S/N ratio, in addition to the effects exerted by the third embodiment.

The dominant cause of noise in optical heterodyne detection is the shot noise, and the noise is proportional to the local light intensity photoelectrically-converted by the photoelectric conversion means 30. Thus, when local light in an optical frequency area where light to be detected is not existent is input to the photoelectric conversion means 30, beat signals are not increased, and shot noises are increased. In the photodetection device of the embodiment, such local light which does not contribute to photodetection is removed by the optical frequency selection means 80, and thus only signal light components adjacent to local light are detected as beat signals, and signal light components not having adjacent local light on the optical frequency axis are not detected. That is, only light to be detected nearly overlapping with a light spectrum of local light selected by the optical frequency selection means 80 is detected as beat signals, which makes it possible to detect a specific optical frequency of light to be detected with high sensitivity and high S/N ratio.

Fifth Embodiment

Figure 6:
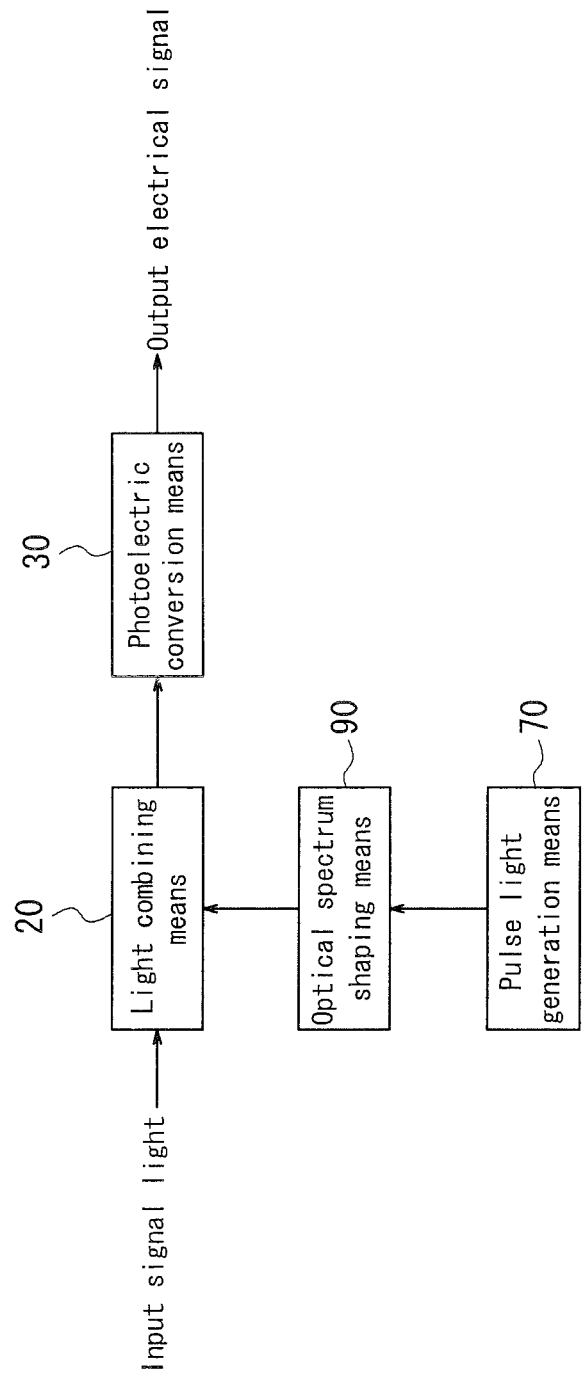
FIG. 6 is a block diagram illustrating a configuration of a main part of the photodetection device according to the fifth embodiment of the invention.

FIG. 6 is a block diagram illustrating a configuration of a main part of the photodetection device according to the fifth embodiment of the invention. With respect to the photodetection device, in the photodetection device having the configuration shown in FIG. 4, there is disposed, between the pulse light generation means 70 and the light combining means 20, an optical spectrum shaping means 90 shaping a light spectrum of output light of the pulse light generation means 70 to a desired shape and outputting it as local light to the light combining means 20.

The optical spectrum shaping means 90 is constituted using a combination of a dielectric multilayer filter, a long-period FBG or a diffraction grating and a liquid-crystal spatial phase modulator, a VIPA waveform shaper or the like. Since other configurations are the same as in FIG. 1, the same components are represented with the same reference symbols, and the description thereof will be omitted.

As above, the optical spectrum shaping means 90 is provided after the pulse light generation means 70 to shape the optical power and the like of a light spectrum of the optical pulse train output to the light combining means 20 into a desired one, which makes it possible to adjust the optical frequency dependency of the photodetection sensitivity, in addition to the effects exerted by the third embodiment. That is, when the optical pulse train is used as local light, the optical frequency dependency of the detection sensitivity occurs depending on the optical spectrum shape of the optical pulse train. Moreover, it is general that the photoelectric conversion means 30 also has the optical frequency dependency of the detection sensitivity. Therefore, as conducted in the embodiment, the optical spectrum shaping means 90 is disposed after the pulse light generation means 70 to shape the light spectrum of the optical pulse train into a desired one and combine it with light to be detected, which makes it possible to adjust the optical frequency dependency of the photodetection sensitivity.

It is noted that the such an optical spectrum shaping means 90 can be disposed before or after the optical frequency selection means 80 in the configuration shown in FIG. 5 so as to constitute a photodetection device, thereby the same effects can be obtained.

Sixth Embodiment

Figure 7:
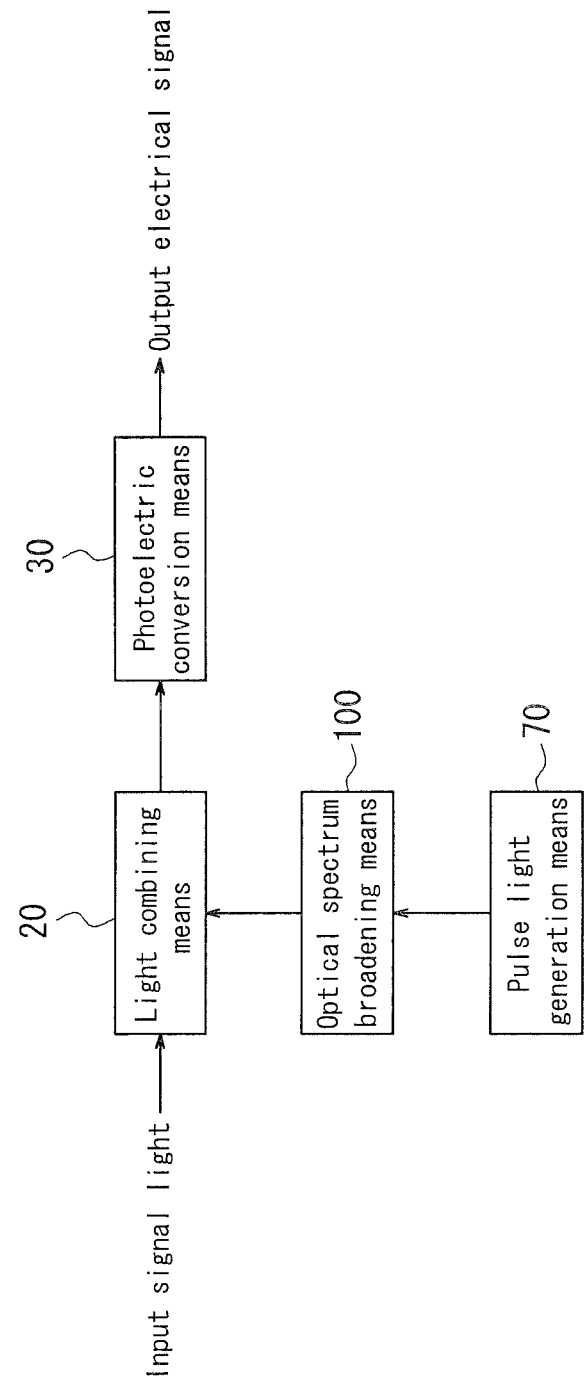
FIG. 7 is a block diagram illustrating a configuration of a main part of the photodetection device according to the sixth embodiment of the invention.

FIG. 7 is a block diagram illustrating a configuration of a main part of the photodetection device according to the sixth embodiment of the invention. With respect to the photodetection device, in the photodetection device having the configuration shown in FIG. 4, there is disposed, between the pulse light generation means 70 and the light combining means 20, an optical spectrum broadening means 100 broadening the light spectrum of the output light of the pulse light generation means 70 and outputting it as local light to the light combining means 20.

The optical spectrum broadening means 100 can be constituted using nonlinear effects in an optical fiber (the optical Kerr effect, the stimulated Raman scattering effect, the stimulated parametric effect) and nonlinear effects in a semiconductor optical amplifier. Since other configurations are the same as in FIG. 1, the same components are represented with the same reference symbols, and the description thereof will be omitted.

As above, the optical spectrum broadening means 100 is provided after the pulse light generation means 70 to broaden a light spectrum of the optical pulse train output to the light combining means 20, which makes it possible to detect even light to be detected with a significantly wide band, in addition to the effects exerted by the third embodiment. That is, when a detection light band of the photoelectric conversion means 30 is sufficiently wide, the detectable optical spectrum band is almost determined based on the optical spectrum band of local light (more precisely, the optical spectrum envelope band of local light) from the pulse light generation means 70. That is, signal light components not overlapping with the light spectrum of local light cannot be detected. In this respect, the optical spectrum broadening means 100 is disposed after the pulse light generation means 70 as in the embodiment, which can broaden the optical spectrum band of the local light and then expand the detectable optical spectrum band, thus enabling detection of even signal light with a significantly wide band.

Seventh Embodiment

Figure 8:
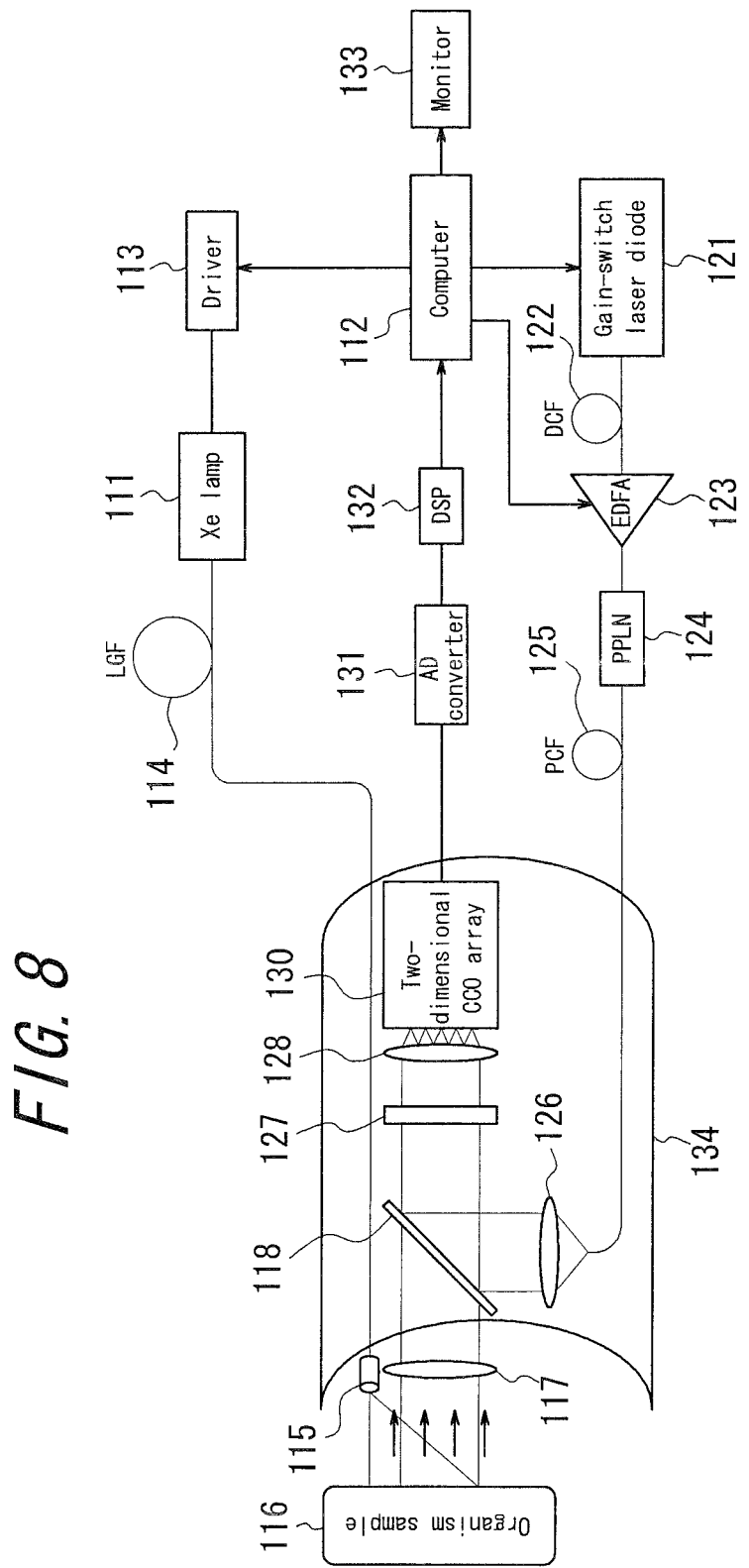
FIG. 8 is a block diagram illustrating a configuration of a main part of the endoscope according to the seventh embodiment of the invention.

FIG. 8 is a block diagram illustrating a configuration of a main part of the endoscope according to the seventh embodiment of the invention. The endoscope observes the inside of body cavities. The endoscope has an Xe lamp 111 as the illumination light source and has the configuration of the photodetection device shown in FIG. 7 as the detection system of light to be detected. In FIG. 8, the Xe lamp 111 is driven by a driver 113 controlled by a computer 112. The light emitted from the Xe lamp 111 passes through a Light Guide Fiber (LGF) 114, and then an organism sample 116 in a body cavity is irradiated therewith from a illuminating lens 115.

The light reflected and scattered by the organism sample 116 through irradiation with illumination light is collected as light to be detected by a collective lens 117 and combined with local light by a combining mirror 118.

As local light, an optical pulse from a gain-switched laser diode 121 is used. The optical pulse from the gain-switched laser diode 121 passes through a Dispersion Compensation Fiber (DCF) 122, an Er-doped Fiber Amplifier (EDFA) 123, a Periodically Poled Lithium Niobate (PPLN) 124, photonic crystal fibers (PCF) 125 as the optical spectrum broadening means and a collimate lens 126, then being incident as local light on a combining mirror 118.

As the gain-switched laser diode 121, there is used a Distributed Feedback Laser Diode (DFB LD) having a wavelength of 1550 nm, for example. A pulse train having a pulse width of 20 ps is obtained from the gain-switched laser diode 121. The repetition rate of the pulse train is controlled by the computer 112 within a range of 1 MHz to 10 GHz. The optical pulse output from the gain-switched laser diode 121 is transmitted through the DCF 122 so that the pulse width is temporally-compressed to about 2 ps and further amplified by the EDFA 123. With respect to the output light of EDFA 123, its wavelength is converted to 775 nm by the PPLN 124, and its light spectrum is broadened by optical Kerr effects after being input to the PCF 125. The output light of the PCF 125 is rendered to be incident on the combining mirror 118 as local light being a parallel beam through the collimate lens 126, and combined with light to be detected. As the PCF 125, there is used one having a zero-dispersion wavelength of 770 nm, a nonlinear coefficient of 100 $W^{-1}km^{-1}$ and a fiber length of 20 m. Thereby, the optical spectrum is broadened to cover a visible band.

Here, the computer 112 controls the repetition rate of the gain-switched laser diode 121 so that it is about twice the signal processing band of the whole photodetection system from the organism sample 116. Furthermore, the computer 112 varies the repetition rate of the gain-switched laser diode 121 and adjusts the optical output average power of the EDFA 123 so that the energy per optical pulse output from the EDFA 123 is not varied. Thereby, the shape of the optical spectrum emitted from the PCF 125 is stabilized.

With respect to the light combined by the combining mirror 118, light other than visible light is removed by the filter 127, and then the resulting light is collected by a collective lens 128 on a two-dimensional CCD array 130 to be photoelectrically-converted. The output electrical signal from the two-dimensional CCD array 130 is converted to digital signals by the AD converter 131, then supplied to the Digital Signal Processor (DSP) 132 to be envelope-detected thereby, and supplied to the computer 112. Then, the computer 112 forms a two-dimensional image based on signals from the DSP 132 and displays it on a monitor 133. It is noted that the illuminating lens 115, the collective lens 117, the combining mirror 118, the collimate lens 126, the filter 127, the collective lens 128 and the two-dimensional CCD array 130 are housed in an endoscope housing 134.

According to the endoscope of the embodiment, optical pulses output from the gain-switched laser diode 121 are temporally-compressed by the DCF 122, amplified by the EDFA 123 and further wavelength-converted by the PPLN 124, thereafter the optical spectrum is broadened by the PCF 125 to obtain local light. Therefore, it is possible to detect light to be detected having a wide band from the organism sample 116 with high sensitivity and high S/N ratio and display it as a two-dimensional image on the monitor 133, thus enabling accurate diagnosis.

Eighth Embodiment

Figure 9:
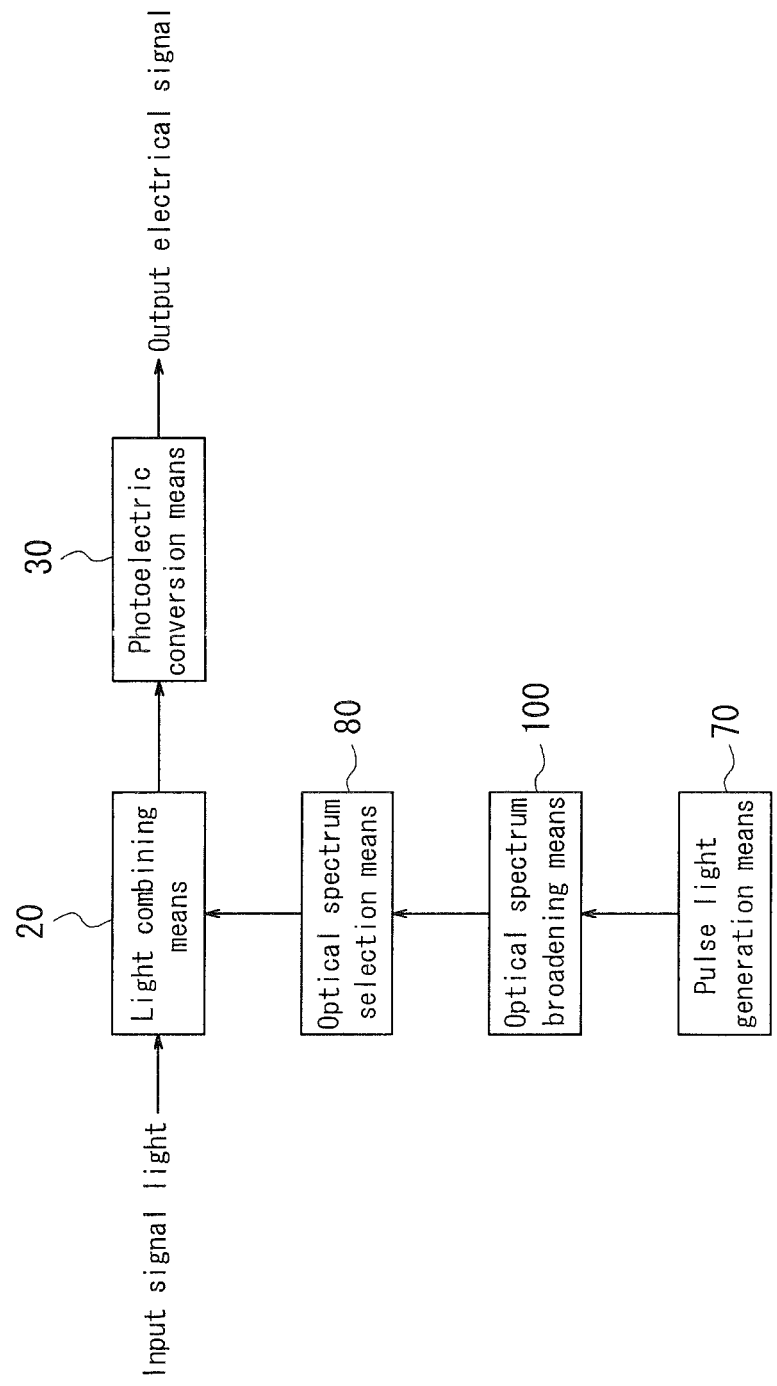
FIG. 9 is a block diagram illustrating a configuration of a main part of the photodetection device according to the eighth embodiment of the invention.

FIG. 9 is a block diagram illustrating a configuration of a main part of the photodetection device according to the eighth embodiment of the invention. With respect to the photodetection device, the optical frequency selection means 80 shown in FIG. 5 and the optical spectrum broadening means 100 shown in FIG. 7 are added to the photodetection device having the configuration shown in FIG. 4 so that the optical spectrum broadening means 100 broadens the optical spectrum of the output light of the pulse light generation means 70 and then the optical frequency selection means 80 selects a required optical frequency as local light from the broadened optical spectrum to output it to the light combining means 20. Since other configurations are the same as in FIG. 1, the same components are represented with the same reference symbols, and the description thereof will be omitted.

Therefore, according to the photodetection device of the embodiment, the same effects as explained in the third, fourth and sixth embodiments can be obtained.

Ninth Embodiment

Figure 10:
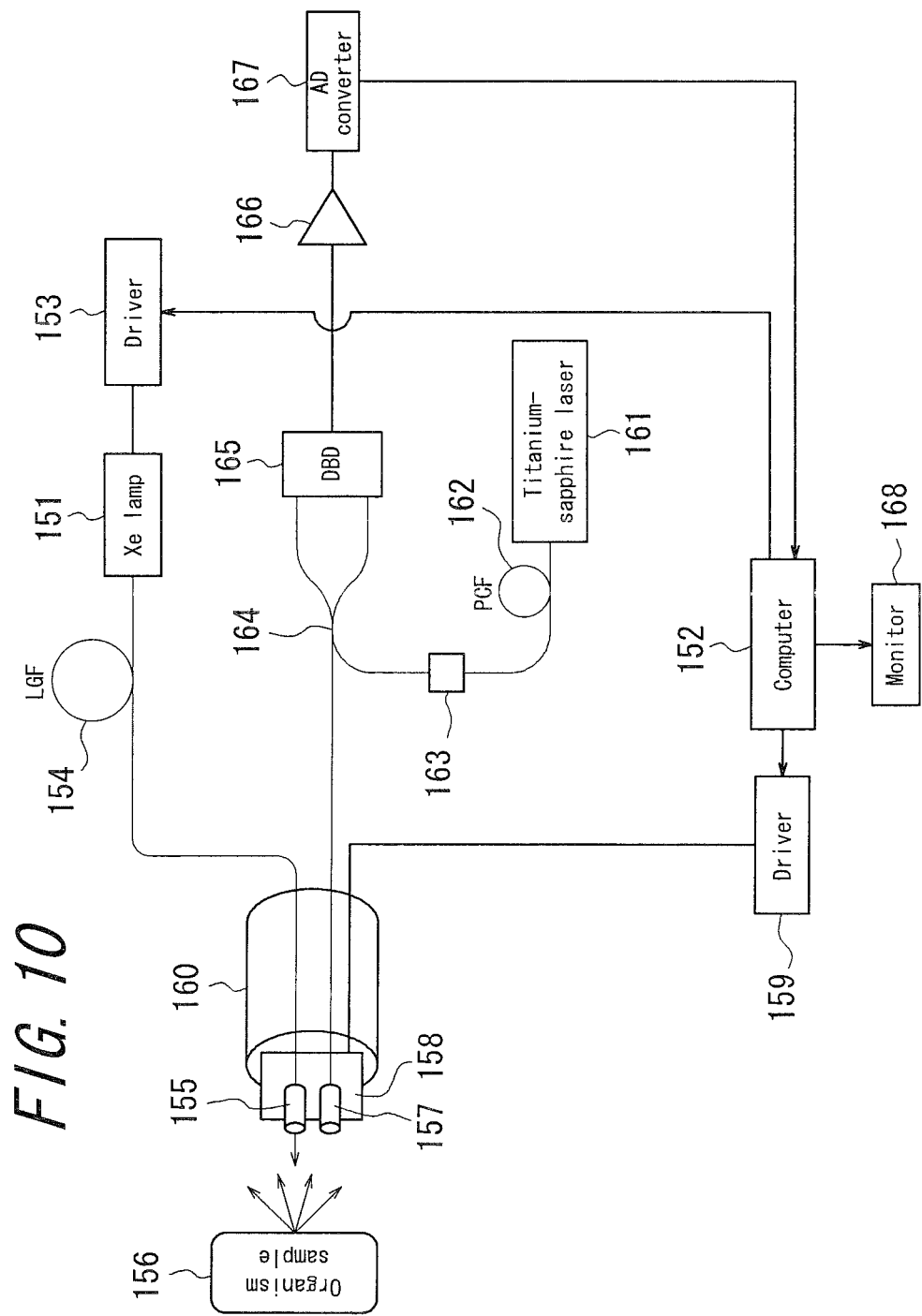
FIG. 10 is a block diagram illustrating a configuration of a main part of the scanning endoscope according to the ninth embodiment of the invention.

FIG. 10 is a block diagram illustrating a configuration of a main part of the scanning endoscope according to the ninth embodiment of the invention. The scanning endoscope scans the inside of body cavities for observation. The scanning endoscope has an Xe lamp 151 as the illumination light source and has the configuration of the photodetection device shown in FIG. 9 as the detection system for light to be detected. In FIG. 10, the Xe lamp 151 is driven by a driver 153 controlled by a computer 152. The light emitted from the Xe lamp 151 passes through a light guide fiber 154, and then an organism sample 156 in a body cavity is irradiated therewith from a collimator 155.

The light reflected and scattered by the organism sample 156 through irradiation with illumination light is collected by a collective lens 157 as light to be detected. Here, the collimator 155 and the collective lens 157 are supported by a scanning mount 158, and the scanning mount 158 is controlled by the computer 152 through a driver 159. The collimator 155, the collective lens 157 and the scanning mount 158 are housed in an endoscope housing 160.

As local light, an optical pulse from a Titanium-sapphire laser 161 is used. The optical pulse from the Titanium-sapphire laser 161 passes through a PCF 162 as the optical spectrum broadening means and an optical filter 163 as the optical frequency selection means, then being incident as local light on an optical fiber coupler 164 as the combining means.

The Titanium-sapphire laser 161 generates ultrashort optical pulses having a repetition rate of 80 MHz, a pulse width of 120 fs, a wavelength of 850 nm and an optical average power of 2.5 W. The ultrashort optical pulses are input to the PCF 162 so that the optical spectrum is broadened. As the PCF 162, there is used one having a zero-dispersion wavelength of 845 nm, a nonlinear coefficient of 70 $W^{-1}$ $km^{-1}$ and a fiber length of 1 m, for example. Then, the optical filter 163 extracts, as local light, light having a wavelength of 450 nm to 700 nm from the optical pulse broadened by the PCF 162 to supply it to the optical fiber coupler 164.

The output light from the collective lens 157 and the local light from the optical filter 163 are combined by the optical fiber coupler 164, and two output from the optical fiber coupler 164 is input to a DBD 165 as the photoelectric conversion means to be photoelectrically-converted. The electrical signals output from the DBD 165 are amplified by an electric amplifier 166, and further an AD converter 167 converts them from analog signals to digital signals and supplies them to the computer 152.

The computer 152 forms a two-dimensional image based on the information obtained from the AD converter 167 while controlling the position of the scanning mount 158 and the optical power of the Xe lamp 151, and displays the resulting two-dimensional image on the monitor 168.

According to the scanning endoscope of the embodiment, the optical spectrum of the optical pulse output from the Titanium-sapphire laser 161 is broadened by the PCF 162 and then incident on the optical filter 163, which makes it possible to easily obtain local light having a desired optical spectrum. Therefore, light to be detected with a wide band from the organism sample 156 can be detected with high sensitivity and high S/N ratio, and displayed as a two-dimensional image on the monitor 168, thus enabling accurate diagnosis.

Tenth Embodiment

Figure 11:
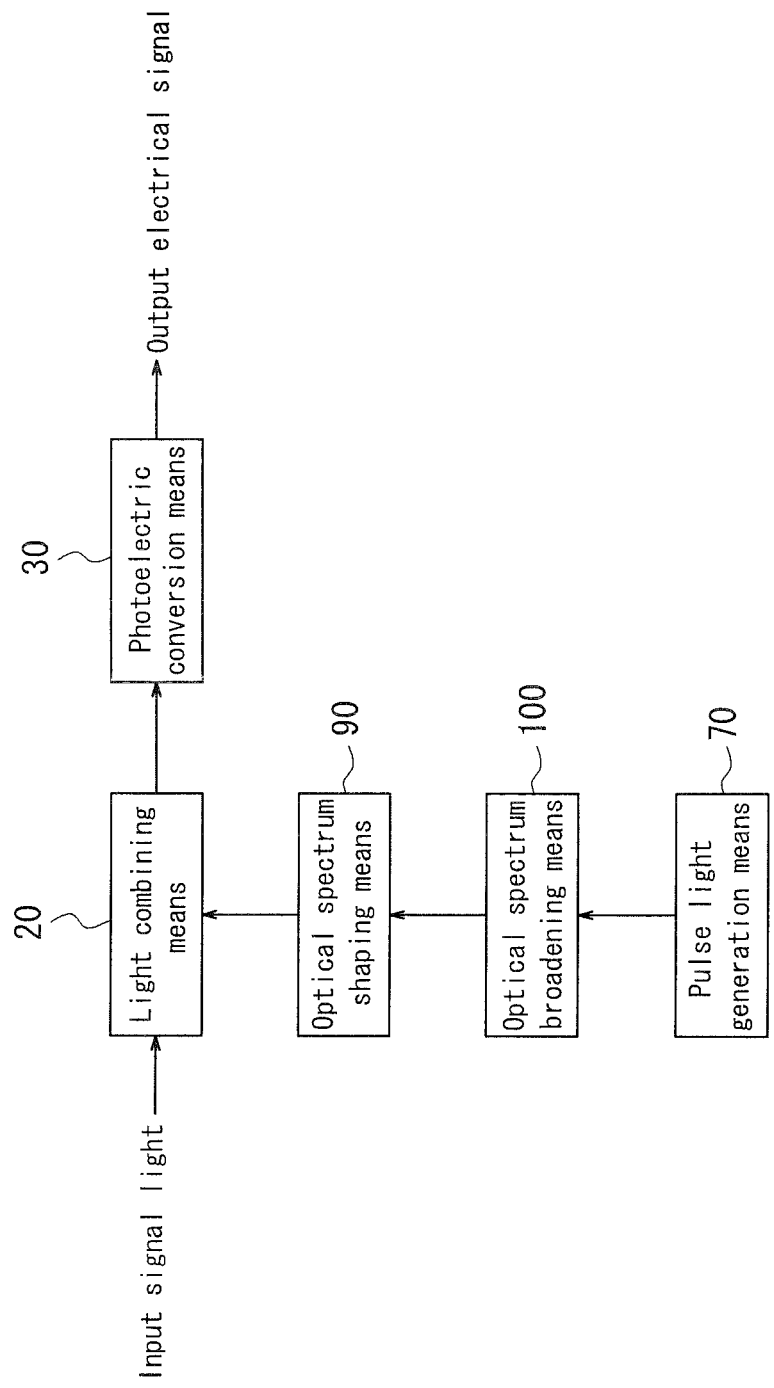
FIG. 11 is a block diagram illustrating a configuration of a main part of the photodetection device according to the tenth embodiment of the invention.

FIG. 11 is a block diagram illustrating a configuration of a main part of the photodetection device according to the tenth embodiment of the invention. With respect to the photodetection device, the optical spectrum shaping means 90 shown in FIG. 6 and the optical spectrum broadening means 100 shown in FIG. 7 are added to the photodetection device having the configuration shown in FIG. 4 so that the light spectrum of the output light of the pulse light generation means 70 is broadened by the optical spectrum broadening means 100 and then the broadend optical spectrum is shaped to a desired shape by the optical spectrum shaping means 90 to be output as local light to the light combining means 20. Since other configurations are the same as in FIG. 1, the same components are represented with the same reference symbols, and the description thereof will be omitted.

Therefore, according to the photodetection device of the embodiment, the same effects as explained in the third, fifth and sixth embodiments can be obtained.

It is noted that the optical frequency selection means 80 shown in FIG. 5 can be disposed before or after the optical spectrum shaping means 90 in the photodetection device shown in FIG. 11, thereby the same effects as described in FIG. 5 can be obtained.

Eleventh Embodiment

Figure 12:
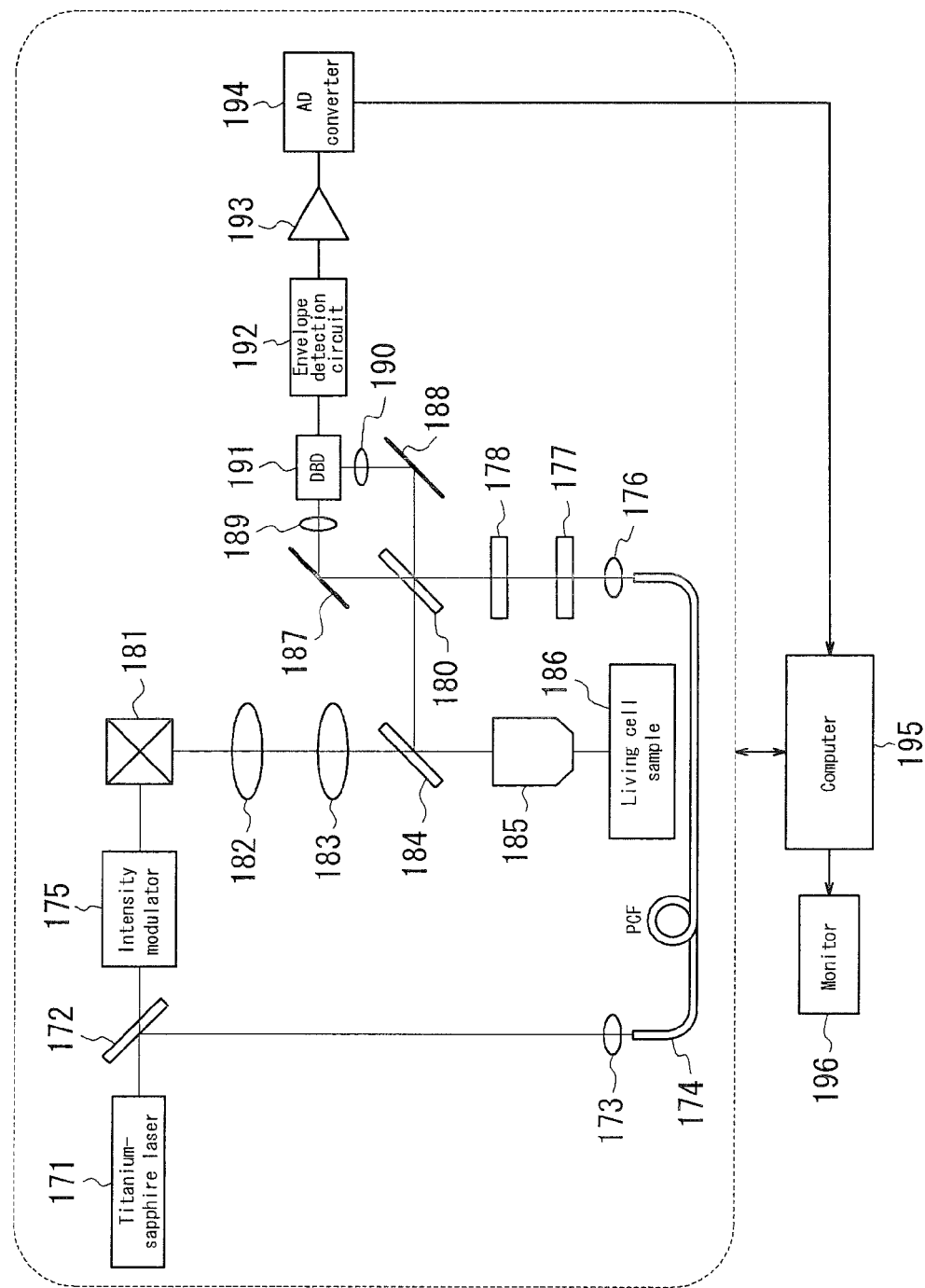
FIG. 12 is a block diagram illustrating a configuration of a main part of the multiphoton fluorescence microscope device according to the eleventh embodiment of the invention.

FIG. 12 is a block diagram illustrating a configuration of a main part of the multiphoton fluorescence microscope device according to the eleventh embodiment of the invention. The multiphoton fluorescence microscope device has a Titanium-sapphire laser 171 as the excitation light source and has the configuration of the photodetection device shown in FIG. 10 as the detection system for light to be detected. In addition, a Titanium-sapphire laser 171 as the excitation light source is used also as the local light source.

The Titanium-sapphire laser 171 generates ultrashort optical pulses having a repetition rate of 80 MHz, a pulse width of 120 fs, a wavelength of 850 nm and an optical average power of 2.5 W, for example. With respect to the ultrashort optical pulses, 90% of light is reflected by a partially reflective mirror 172, and the reflected light passes through a lens 173 to be input to a PCF 174 as the optical spectrum broadening means. On the other hand, the remaining 10% of light transmitting through the partially reflective mirror 172 is input to a light intensity regulator 175.

As the PCF 174, there is used one having a zero-dispersion wavelength of 845 nm, a nonlinear coefficient of 70 $W^{-1} km^{-1}$ and a fiber length of 1 m to broaden the optical spectrum of input ultrashort optical pulses. Here, a number of ripples occur in the optical spectrum broadened by the PCF 174. Thus, the optical pulse output from the PCF 174 is rendered to be incident, after passing through a lens 176, on a dielectric-multilayer optical spectrum shaping filter 177 as the optical spectrum shaping means so that the optical spectrum is shaped.

As the optical spectrum shaping filter 177, there is used that of, for example, dielectric multilayer type having transmissive properties of flattening the ripples with a wavelength of 500 nm to 600 nm on the broadened optical spectrum. The optical pulse whose optical spectrum has been shaped by the optical spectrum shaping filter 177 passes through an optical band-pass filter 178 allowing light having a wavelength of 500 nm to 600 nm to pass therethrough, then being incident as local light on a half mirror 180 as the light combining means.

With respect to the light having passed through the partially reflective mirror 172, on the other hand, its average light intensity is adjusted to 100 mW by the light intensity regulator 175. Then, the resulting light passes through an X-Y galvano scanner mirror 181, a pupil lens 182, a tube lens 183, a dichroic mirror 184 and an objective lens 185, and is collected so that a living cell sample 186 to be inspected is irradiated therewith. Thereby, the eGFP, for example, in the living cell sample 186 is multiphoton-excited (two-photon-excited, for example) so that fluorescence is generated.

The fluorescence generated from the living cell sample 186 passes through the objective lens 185 to the dichroic mirror 184. The dichroic mirror 184 is configured so as to allow light having a wavelength of 850 nm from the Titanium-sapphire laser 171 to pass therethrough and so as to reflect light having a short wavelength of 700 nm or shorter. Thus, fluorescence having a wavelength of about 500 nm to 600 nm generated in the living cell sample 186 is reflected by the dichroic mirror 184.

The fluorescence having a wavelength of 500 nm to 600 nm reflected by the dichroic mirror 184 is combined with local light output from the optical band-pass filter 178 by the half mirror 180. Two combined output obtained from the half mirror 180 passes through a reflective mirror 187, 188, and a lens 189, 190, respectively, to a DBD 191 as the photoelectric conversion means constituted by the SiPD to be photoelectrically-converted. The electrical signals output from the DBD 191 are envelope-detected by an envelope detection circuit 192, then amplified by an electric amplifier 193 and, further, converted by an AD converter 194 from analog signals to digital signals to be supplied to a computer 195.

The computer 195 controls the whole of multiphoton fluorescence microscope device to process output obtained from the AD converter 194 and displays the fluorescence image on a monitor 196.

According to the multiphoton fluorescence microscope device of the embodiment, the Titanium-sapphire laser 171 as the excitation light source is used also as the local light source so that a part of the amount of excitation light emitted from the Titanium-sapphire laser 171 is split for local light. Then, the optical spectrum of the divided optical pulses for local light is broadened by the PCF 174 and, further, the optical spectrum is shaped by the optical spectrum shaping filter 177 to obtain local light, which makes it possible to detect fluorescence from the living cell sample 186 with high sensitivity and high S/N ratio with simple construction.

It is noted that the invention is not limited to the above embodiments, and many variations and modifications can be implemented. For example, the photodetection device according to the invention can be effectively applied when signal light to be detected is not only reflected light, scattered light and fluorescence from a sample but also transmissive light or phosphorescence. Moreover, illumination light in detecting reflected light, scattered light or transmissive light is not limited to lamp light and it may be LED (Light Emitting Diode) light. Furthermore, the optical spectrum shaping means shown in FIG. 6 can be provided before or after the optical frequency selection means in FIGS. 5, 9 and 10.

Moreover, the invention can be applied for photodetection of electromagnetic waves from ultraviolet rays having a wavelength of about 180 nm to infrared rays having a wavelength of about 50 and it is not limited to detection of visible light as described in the above embodiments. For example, when ultraviolet rays are to be detected, a Titanium-sapphire laser, for example, is used as the local light generation means, and Xenon gas is irradiated with high-optical-power ultrashort optical pulses generated from the Titanium-sapphire laser so that a higher-order harmonic wave is generated in Xenon gas, thereby ultrashort optical pulses obtained in an ultraviolet range are used as local light for ultraviolet detection. Moreover, the light combining means is constituted using a multilayer mirror, for example, and the photoelectric conversion means is constituted using the PMT, for example.

Moreover, when infrared rays are to be detected, there is used, as the local light generation means, a mode locked Nd: YAG laser, for example, so that the intense picosecond optical pulse generated from the mode locked Nd: YAG laser is incident on the PPLN, thereby the optical pulse with an infrared wavelength obtained through difference-frequency mixing in the PPLN is used as local light for infrared detection. Moreover, the light combining means can be constituted using a CsI substrate beam splitter, for example, and the photoelectric conversion means is constituted using a photoconductive element with Ge:Zn, for example.

Figure 13:
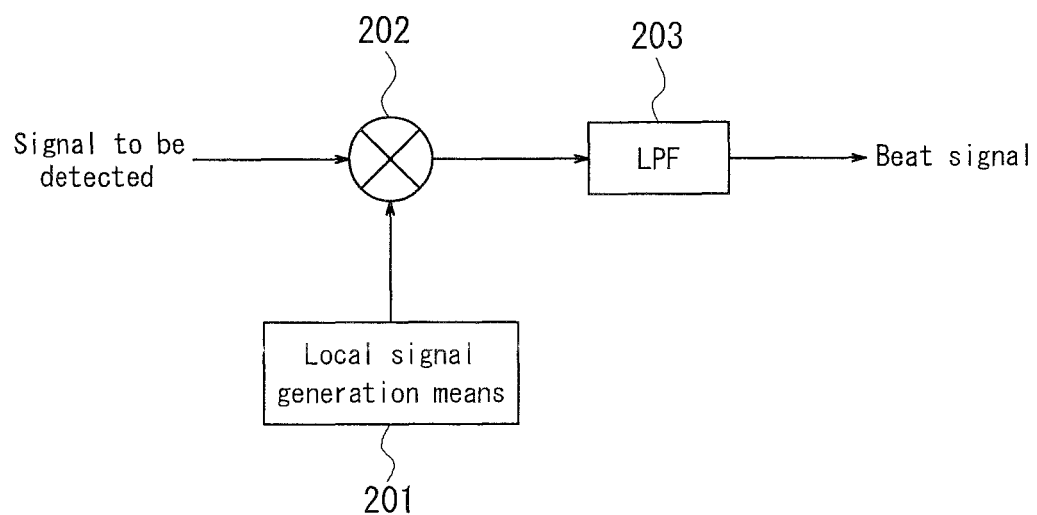
FIG. 13 is a block diagram illustrating a basic configuration of an electromagnetic wave detection device when detecting electromagnetic waves other than light.

Moreover, the invention can be applied effectively in detection of electromagnetic waves other than light: radio waves, X-rays, γ-rays and so on, for example. In such a case, as shown in FIG. 13, for example, a local signal generation means 201 generates local signals having a plurality of frequency components in a frequency band of signals to be detected based on electromagnetic waves to be detected (radio waves, for example) within a given period of time, and a mixer 202 mixes the local signal and signal to be detected. Then, a Low Pass Filter (LPF) 203 extracts beat signals from the output of the mixer 202 so that signals to be detected based on electromagnetic waves to be detected are detected on the basis of the beat signals. Therefore, the invention can be understood as described in the following note.

Note (Item 1) An electromagnetic wave detection device, comprising a local signal generation means generating a local signal having a plurality of frequency components in a frequency band of a signal to be detected based on an electromagnetic wave to be detected within a given period of time;

a mixture means mixing the local signal generated from the local signal generation means and the signal to be detected; and a low pass filter extracting a beat signal from an output of the mixture means, wherein the signal to be detected is heterodyne-detected based on the beat signal.

(Item 2) An electromagnetic wave detection device according to the item 1, wherein the local signal generation means comprises a plurality of signal generation sources generating continuous signals with a respectively different frequency.

(Item 3) An electromagnetic wave detection device according to the item 1, wherein the local signal generation means is constituted by a pulse generation means generating a pulse train.

(Item 4) An electromagnetic wave detection device according to the item 3, wherein the local signal generation means further comprises a filter means selecting a given frequency component as a local signal from an output of the pulse generation means.

(Item 5) An electromagnetic wave detection device according to the item 3, wherein the local signal generation means further comprises a spectrum shaping means shaping a spectrum of an output of the pulse generation means.

(Item 6) An electromagnetic wave detection device according to the item 3, wherein the local signal generation means further comprises a spectrum broadening means broadening a spectrum of an output of the pulse generation means.

(Item 7) An electromagnetic wave detection device according to the item 6, wherein the local signal generation means further comprises a filter means selecting a given frequency component as a local signal from an output of the spectrum broadening means.

(Item 8) An electromagnetic wave detection device according to the item 6, wherein the local signal generation means further comprises a spectrum shaping means shaping a spectrum of an output of the spectrum broadening means.

(Item 9) An electromagnetic wave detection device according to any one of the items 3 to 8, wherein the pulse generation means generates the pulse train at a repetition rate being twice or more a signal processing frequency band processing an output of the low pass filter.

(Item 10) An electromagnetic wave detection device according to any one of the items 1 to 9, further comprising an envelope detection means detecting an envelope of the beat signal.

(Item 11) An electromagnetic wave detection method, comprising a step of generating a local signal having a plurality of frequency components in a frequency band of a signal to be detected based on an electromagnetic wave to be detected within a given period of time;

a step of mixing the signal to be detected and the local signal; and a step of extracting a beat signal from the mixed signal, wherein the signal to be detected is heterodyne-detected based on the beat signal.

(Item 12) A microscope detecting electromagnetic waves to be detected from a sample to be observed, comprising an electromagnetic wave detection device according to any one of the items 1 to 10, wherein the electromagnetic wave detection device heterodyne-detects a signal to be detected based on the electromagnetic wave to be detected from the sample to be observed.

(Item 13) An endoscope detecting electromagnetic waves to be detected from an inside of a body cavity and observing the inside of the body cavity, comprising an electromagnetic wave detection device according to any one of the items 1 to 10, wherein the electromagnetic wave detection device heterodyne-detects a signal to be detected based on the electromagnetic wave to be detected from the inside of the body cavity.

The invention claimed is:

1. A photodetection device for detecting light to be detected, comprising a local light generation unit generating local light having a plurality of optical frequency components in an optical frequency band of the light to be detected within a given period of time;

a light combining unit combining the local light generated from the local light generation unit and the light to be detected; and a photoelectric conversion unit photoelectrically-converting light output from the light combining unit and generating a beat signal of the local light and the light to be detected, wherein the light to be detected, having a low temporal coherence, is heterodyne-detected based on an output of the photoelectric conversion unit.

2. A photodetection device according to claim 1, wherein the local light generation unit comprises a plurality of light generation sources generating continuous light with a respectively different optical frequency.

3. A photodetection device according to claim 1, wherein the local light generation unit is constituted by an optical pulse generation unit generating an optical pulse train.

4. A photodetection device according to claim 3, wherein the local light generation unit further comprises an optical filter unit selecting a given optical frequency component as local light from output light of the optical pulse generation unit.

5. A photodetection device according to claim 3, wherein the local light generation unit further comprises an optical spectrum shaping unit shaping a spectrum of output light of the optical pulse generation unit.

6. A photodetection device according to claim 3, wherein the local light generation unit further comprises an optical spectrum broadening unit broadening a spectrum of output light of the optical pulse generation unit.

7. A photodetection device according to claim 6, wherein the local light generation unit further comprises an optical filter unit selecting a given optical frequency component as local light from output light of the optical spectrum broadening unit.

8. A photodetection device according to claim 6, wherein the local light generation unit further comprises an optical spectrum shaping unit shaping a spectrum of output light of the optical spectrum broadening unit.

9. A photodetection device according to claim 3, wherein the optical pulse generation unit generates the optical pulse train at a repetition rate being twice or more a signal processing frequency band processing an output of the photoelectric conversion unit.

10. A photodetection device according to claim 3, wherein the optical pulse generation unit comprises a mode locked laser.

11. A photodetection device according to claim 3, wherein the optical pulse generation unit comprises a gain-switched laser or a Q-switched laser.

12. A photodetection device according to claim 1, further comprising an envelope detection unit detecting an envelope of an output of the photoelectric conversion unit.

13. A photodetection method for detecting light to be detected, comprising
    a local light generation step generating local light having a plurality of optical frequency components in an optical frequency band of the light to be detected within a given period of time;
    a combining step combining the light to be detected and the local light; and
    a photoelectric conversion step photoelectrically-converting the combined light and generating a beat signal of the local light and the light to be detected,
    wherein the light to be detected, having a low temporal coherence, is heterodyne-detected based on the beat signal.

14. A microscope detecting light to be detected from a sample to be observed, comprising
    a photodetection device according to claim 1,
    wherein the photodetection device heterodyne-detects the light to be detected from the sample to be observed.

15. An endoscope detecting light to be detected from an inside of a body cavity and observing the inside of the body cavity, comprising
    a photodetection device according to claim 1,
    wherein the photodetection device heterodyne-detects the light to be detected from the inside of the body cavity.

* * * * *